United States Patent
Brousmiche et al.

(10) Patent No.: US 9,482,603 B2
(45) Date of Patent: Nov. 1, 2016

(54) SOLID PHASE EXTRACTION DEVICE FOR DRIED SAMPLE CARDS

(71) Applicant: Waters Technologies Corporation, Milford, MA (US)

(72) Inventors: Darryl W. Brousmiche, Grafton, MA (US); Pamela C. Iraneta, Brighton, MA (US); Erin E. Chambers, North Brookfield, MA (US); Moon Chul Jung, Arlington, MA (US)

(73) Assignee: Waters Technologies Corporation, Milford, MA (US)

( * ) Notice: Subject to any disclaimer, the term of this patent is extended or adjusted under 35 U.S.C. 154(b) by 9 days.

(21) Appl. No.: 14/345,009

(22) PCT Filed: Sep. 18, 2012

(86) PCT No.: PCT/US2012/055853
§ 371 (c)(1),
(2) Date: Mar. 14, 2014

(87) PCT Pub. No.: WO2013/043562
PCT Pub. Date: Mar. 28, 2013

(65) Prior Publication Data
US 2014/0366656 A1 Dec. 18, 2014

Related U.S. Application Data

(60) Provisional application No. 61/538,224, filed on Sep. 23, 2011.

(51) Int. Cl.
*B01L 3/00* (2006.01)
*G01N 1/40* (2006.01)
(Continued)

(52) U.S. Cl.
CPC ............. *G01N 1/405* (2013.01); *B01L 3/5021* (2013.01); *B01L 3/5085* (2013.01); *B01L 3/523* (2013.01);
(Continued)

(58) Field of Classification Search
CPC ............. B01L 3/505; G01N 1/20; G01N 1/12
USPC .................... 73/864.91, 863, 864.51, 864.62
See application file for complete search history.

(56) References Cited

U.S. PATENT DOCUMENTS

| | | | |
|---|---|---|---|
| 6,723,236 B2 * | 4/2004 | Fisk | B01D 15/424 210/198.2 |
| 7,052,611 B2 | 5/2006 | Fisk | |

(Continued)

FOREIGN PATENT DOCUMENTS

| | | |
|---|---|---|
| JP | S63171337 A | 7/1988 |
| JP | H10104226 A | 4/1998 |

(Continued)

OTHER PUBLICATIONS

International Search Report & Written Opinion in related international patent application No. PCT/US12/55853, mailed on Dec. 3, 2012; 8 pages.

(Continued)

*Primary Examiner* — Lisa Caputo
*Assistant Examiner* — Nigel Plumb
(74) *Attorney, Agent, or Firm* — Schmeiser, Olsen & Watts LLP; William G. Goerin

(57) ABSTRACT

Described is a device for solid phase extraction of a dried sample of a biological fluid. The device includes a support structure such as a plate or support block that has a first side to receive a dried sample card. The support structure also has a second side that is opposite the first side and a number of apertures that extend between the first and second sides. The device also includes a plurality of wells each containing a sample preparation material and having an inlet end that communicates with a respective aperture at the second side of the support structure. Each dried sample on the dried sample card is aligned with one of the apertures. Extraction samples in each well pass through the sample preparation material, such as a chromatographic sorbent, in the well to remove one or more constituents of the extraction sample.

11 Claims, 6 Drawing Sheets

(51) Int. Cl.
*B01L 7/00* (2006.01)
*B01L 9/06* (2006.01)
*B01L 9/00* (2006.01)
G01N 1/28 (2006.01)
B01L 3/02 (2006.01)

(52) U.S. Cl.
CPC .. B01L 7/52 (2013.01); B01L 9/06 (2013.01); B01L 9/52 (2013.01); G01N 1/4055 (2013.01); B01L 3/0217 (2013.01); B01L 3/5023 (2013.01); B01L 2200/028 (2013.01); B01L 2200/0631 (2013.01); B01L 2200/0647 (2013.01); B01L 2200/0684 (2013.01); B01L 2200/0689 (2013.01); B01L 2200/082 (2013.01); B01L 2200/141 (2013.01); B01L 2200/16 (2013.01); B01L 2300/044 (2013.01); B01L 2300/069 (2013.01); B01L 2300/0681 (2013.01); B01L 2300/0816 (2013.01); B01L 2300/0829 (2013.01); B01L 2400/043 (2013.01); B01L 2400/0409 (2013.01); B01L 2400/0677 (2013.01); G01N 2001/288 (2013.01); G01N 2001/4061 (2013.01)

(56) References Cited

U.S. PATENT DOCUMENTS

| | | | | |
|---|---|---|---|---|
| 7,093,508 | B2* | 8/2006 | Harris | B01L 99/00 73/864 |
| 2002/0155034 | A1* | 10/2002 | Perman | B01L 3/50255 422/69 |
| 2004/0246289 | A1* | 12/2004 | Parnow | B41J 2/2135 347/19 |
| 2011/0011503 | A1* | 1/2011 | Parker | A45C 3/08 150/104 |
| 2011/0111503 | A1 | 5/2011 | Siedel et al. | |
| 2011/0129863 | A1* | 6/2011 | Shoemaker | B01L 3/50255 435/29 |
| 2011/0129940 | A1* | 6/2011 | Gijlers | B01L 3/505 436/178 |
| 2011/0132111 | A1* | 6/2011 | Shoemaker | G01N 1/286 73/864.41 |
| 2011/0136251 | A1* | 6/2011 | Astle | B01L 3/0275 436/178 |
| 2013/0116597 | A1* | 5/2013 | Rudge | A61B 5/150358 600/575 |

FOREIGN PATENT DOCUMENTS

| | | |
|---|---|---|
| JP | 2001116749 A | 4/2001 |
| JP | 2002243726 A | 8/2002 |
| JP | 2002531258 A | 9/2002 |
| JP | 2005521041 A | 7/2005 |
| JP | 2013513097 A | 4/2013 |
| JP | 2013513100 A | 4/2013 |
| WO | 0014532 A1 | 3/2000 |
| WO | 2011067221 A1 | 6/2011 |
| WO | 2011067309 A1 | 6/2011 |
| WO | 2013067520 A1 | 5/2013 |

OTHER PUBLICATIONS

Deglon, et al., "On-line desorption of dried blood spot: A novel approach for the direct LC/MS analysis of mu-whole blood samples", Journal of Pharmaceutical and Biological Analysis 49, Feb. 2009, pp. 1034-1039.

Extended European Search Report in counterpart European Patent Application No. 12834029.6, mailed on Apr. 7, 2015; 8 pages.

International Preliminary Report on Patentability in counterpart international patent application No. PCT/US12/55853, mailed on Apr. 3, 2014; 7 pages.

Notice of Rejection in counterpart Japanese Patent Application No. 2014-531899, mailed on Aug. 23, 2016; 9 pages.

* cited by examiner

SOLID PHASE EXTRACTION DEVICE FOR DRIED SAMPLE CARDS

RELATED APPLICATION

This application claims the benefit of the earlier filing date of U.S. Provisional Patent Application Ser. No. 61/538,224, filed Sep. 23, 2011 and titled "Solid Phase Extraction Device for Dried Sample Cards," the entirety of which is incorporated herein by reference.

FIELD OF THE INVENTION

The invention relates generally to analyses of dried biological fluids. More particularly, the invention relates to a device to facilitate analysis of samples reconstituted from dried sample spots, such as dried blood spots, on a collection medium or sample carrier, such as a dried blood spot card.

BACKGROUND

Measuring concentrations of administered drugs and their metabolites in biological fluids, such as whole blood, plasma and serum, is important to understanding the efficacy and toxicological effects of the drugs. Typical clinical studies require handling and processing large numbers of biological fluid samples at low temperature with special care. Dried spot sampling is an alternative practice that is based on collection of small volumes (e.g., several microliters or less) of biological fluids as dried spots. For example, dried blood spot (DBS) sampling involves the collection of small volumes of blood onto a carrier medium. Samples are later reconstituted from the dried spots using suitable solvents during an extraction process. The reconstituted samples can be analyzed, for example, in a liquid chromatography—mass spectrometry (LC-MS) assay. In many instances, the analysis of reconstituted samples is adversely affected by the presence of interfering elements in the sample matrix.

Solid phase extraction (SPE) is a chromatographic technique for preparing samples prior to performing quantitative analysis, for example, using high performance liquid chromatography (HPLC) or ultra performance liquid chromatography (UPLC). The goal of SPE is to isolate target analytes from a complex sample matrix containing unwanted interferences that can have a negative effect on the ability to perform quantitative analysis. The isolated target analytes are recovered in a solution that is compatible with quantitative analysis. The solution containing the target compound can be directly used for analysis. Alternatively, further processing can be performed, for example, by evaporation and reconstitution using another solution of a lesser volume to further concentrate the target compound and make it more amenable to detection and measurement.

SUMMARY

In one aspect, the invention features a device for solid phase extraction of a dried sample of a biological fluid. The device includes a support structure having a first side to receive a dried sample card having a plurality of dried samples of a biological fluid. The support structure also has a second side that is opposite to the first side and has a plurality of apertures between the first and second sides. The support structure is configured to hold a received dried sample card in a position wherein each of the dried samples is adjacent to one of the apertures. The device also includes a plurality of wells each having an inlet end in communication with one of the apertures on the second side of the support structure and each having an outlet end. The device further includes a sample preparation material disposed in at least one of the wells.

In another aspect, the invention features a method for solid phase extraction of a dried sample of a biological fluid. The method includes securing a dried sample card having a plurality of dried samples of a biological fluid to a solid phase extraction device. The solid phase extraction device includes a support structure having a first side to receive a dried sample card having a plurality of dried samples of a biological fluid. The support structure has a second side opposite the first side and a plurality of apertures between the first and second sides. The support structure is configured to hold a received dried sample card in a position wherein each of the dried samples is adjacent to one of the apertures. The solid phase extraction device also includes a plurality of wells each having an inlet end in communication with one of the apertures on the extraction side of the support structure and each having an outlet end. The solid phase extraction device further includes a sample preparation material disposed in each of the wells. For each of the dried samples and a respective one of the wells, an extraction solvent flows through the dried sample and into the well to thereby generate an extraction sample. Each extraction sample is passed through the sample preparation material of the well to remove at least one constituent from the extraction sample.

In yet another aspect, the invention features a method for solid phase extraction of a dried sample of a biological fluid. The method includes securing a dried sample card having a plurality of dried samples of a biological fluid to a solid phase extraction device. The solid phase extraction device includes a support structure having a first side to receive a dried sample card having a plurality of dried samples of a biological fluid. The support structure has a second side opposite the first side and a plurality of apertures between the first and second sides. The support structure is configured to hold a received dried sample card in a position wherein each of the dried samples is adjacent to one of the apertures. The solid phase extraction device also includes a plurality of wells each having an inlet end in communication with one of the apertures on the second side of the support structure and each having an outlet end. The solid phase extraction device further includes a sample preparation material disposed in each of the wells. Portions of the dried sample card are separated from a remainder of the dried sample card to cause each of the dried samples to be disposed in one of the wells. An extraction solvent is supplied to each of the wells to thereby create extraction samples. Each extraction sample is passed through the sample preparation material of the well to remove at least one constituent from the extraction sample.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Figure 1A:
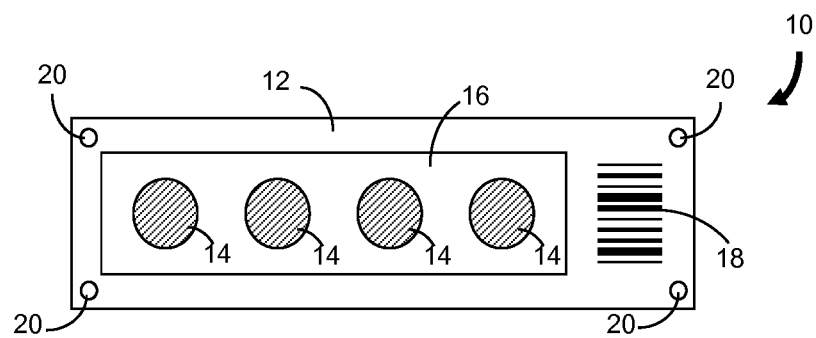
FIG. 1A and FIG. 1B show a top view and a cross-sectional side view, respectively, of an embodiment of a DBS card suitable for storing dried samples of blood that can be used with embodiments of a SPE device according to the invention.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

In brief overview, embodiments of the invention include a device for solid phase extraction of a dried sample of a biological fluid. In some embodiments, the device includes a support structure such as a plate or support block that has a first side to receive a dried sample card. The support structure also has a second side that is opposite the first side and a number of apertures that extend between the first and second sides. Each dried sample on a received dried sample card is aligned with one of the apertures or channels. The device includes a number of wells each having an inlet end and an outlet end. Each well contains a sample preparation material such as a chromatographic sorbent. The inlet end of each well communicates with a respective aperture at the second side of the support structure.

Advantageously, the SPE device maintains the ease of use of dried sample cards at the time of sampling and the inexpensive shipping of the cards. At the test location, a dried sample card is fitted into the device to permit convenient sample extraction and sample preparation or cleanup, such as the removal of phospholipids from blood samples. For example, some embodiments of the device utilize a piston mechanism to perform whole spot punching. Sample extraction and preparation can be performed using the punched sample. Alternative embodiments of the device permit convenient inline sample extraction by face seal elution with subsequent sample preparation. The extraction sample received at the inlet end of each well passes through a chromatographic sorbent disposed in the well before exiting the well, thereby removing one or more constituents of the extraction sample. The extraction sample at the outlet end of the well can be further processed or used directly for quantitative analysis. Automated extraction and sample preparation performed with the device can yield improved reproducibility relative to conventional extraction and preparation techniques.

Figure 1B:
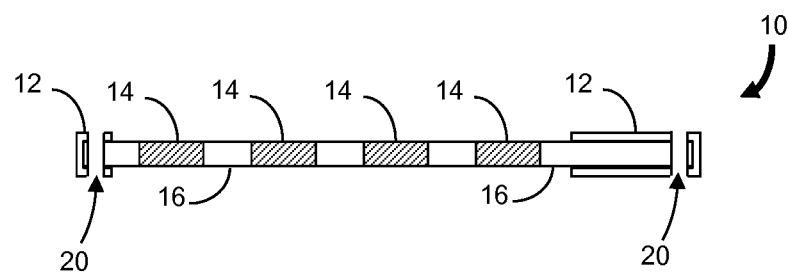

Dried spot sampling is based on the collection of small volumes of biological fluids as dried spots on an appropriate carrier medium. FIG. 1A and FIG. 1B show a top view and a cross-sectional side view, respectively, of an embodiment of a DBS card 10 suitable for storing dried samples of blood that can be used with embodiments of a SPE device according to the invention. In the following example, the DBS card 10 is constructed according to principles disclosed in PCT Patent Application Publication No. WO/2011/153122 titled "Apparatus and Methods for Preparation and Analysis of Dried Samples of a Biological Fluid" although those of skill in the art will recognize that the SPE device can be adapted for use with other types of dried sample cards of varying sizes and formats.

The illustrated DBS card 10 includes a frame 12 having a rectangular opening to expose a carrier medium having four collection regions 14 surrounded by an impermeable region 16 although in other embodiments the collection regions 14 are not surrounded by regions impregnated with impermeable material. The frame 12 is preferably a rigid structure such as cardboard that provides a means for holding the DBS card 10 without contaminating or disturbing the samples in the collection regions 14. The frame 12 may include a bar code 18, matrix bar code or other visible identification scheme by which to identify a particular DBS card. The frame 12 includes alignment holes 20 near each of the four corners. The carrier medium is a filter paper or other material capable of absorbing a biological fluid. The impermeable region 16 is created, for example, by printing an ink or other substance into the carrier medium in a predetermined pattern to define the collection regions 14. The printed substance fills the pores of the filter paper and prevents fluids from being absorbed in the area of the pattern. Thus a sample applied to a collection region 14 is prevented from spreading into the surrounding impermeable region 16. The volume of fluid that is contained within each collection region 14 can be accurately defined and is based upon the dimensions (e.g., thickness and diameter) of the region 14 and the physical properties of the carrier medium (e.g., porosity). By way of examples, the ink or printable substance can be a wax, photoresist, sol-gel precursor or polymer precursor. In some embodiments, a hydrophobic ink that is impermeable to aqueous biological fluids is used to create the impermeable pattern in the carrier medium.

Figure 2A:
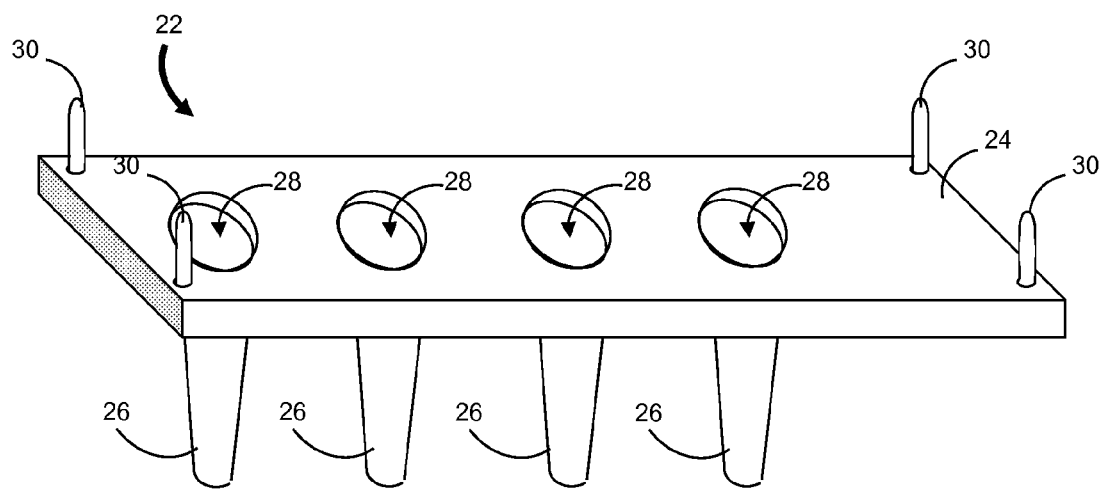
FIGS. 2A, 2B and 2C show a perspective view, top view and cross-sectional side view, respectively, of one embodiment of an SPE device according to the invention.
Figure 2B:
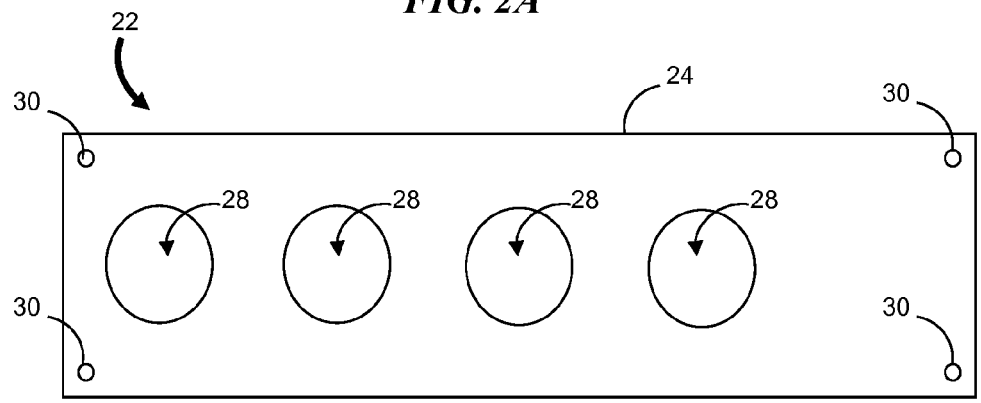
Figure 2C:
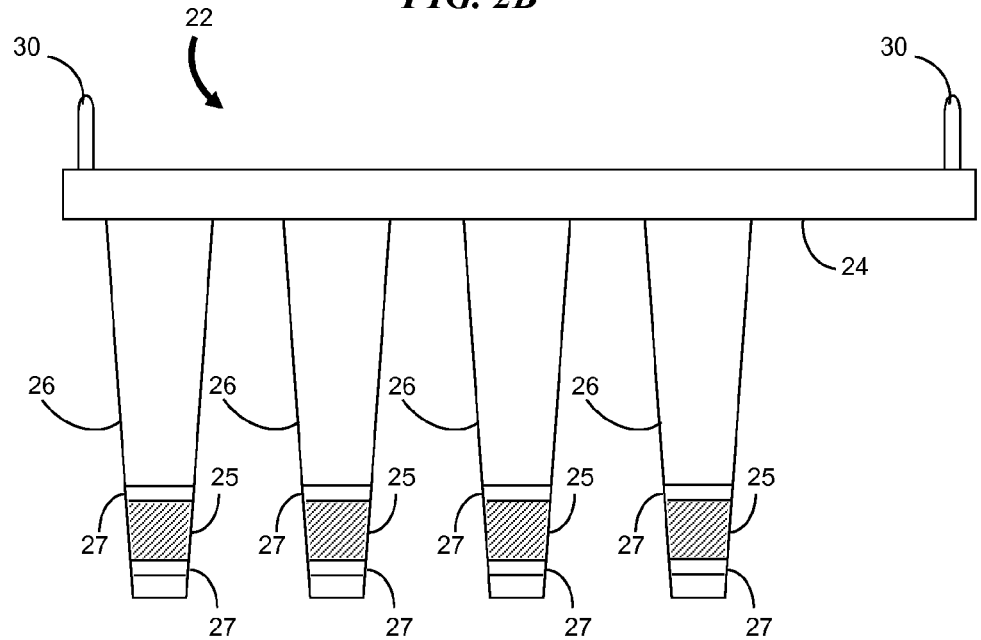

FIGS. 2A, 2B and 2C show a perspective view, top view and cross-sectional side view, respectively, of one embodiment of an SPE device 22 according to principles of the invention. The SPE device 22 includes a support structure in the form of a plate 24 and also includes four wells 26 arranged in a linear configuration. Each well 26 has an inlet end in communication with a plate aperture 28 and an outlet end to direct fluid that passes through the well 26 into a suitable collection container (not shown). In the illustrated embodiment, the wall of each well 26 is tapered such that the diameter of the inlet end is greater than the diameter at the outlet end although this is not a requirement.

Each well 26 includes a sample preparation material 25 such as a chromatographic sorbent. The sorbent 25 may be contained between a pair of porous filters 27 disposed in the well 26. The sorbent can include particulate matter (e.g., a packed particle bed) that is adhered to by at least one target substance or interfering substance. Alternatively, the sorbent can be a monolithic structure which may or not be provided between porous filters.

The illustrated SPE device 22 is adapted for receiving and securing the DBS card 10 of FIG. 1 in position against the plate 24 such that the collection regions 14 are centered over the plate apertures 28. Proper lateral alignment of the collection regions 14 to the apertures 28 is achieved using four alignment pins 30 that extend upward from the plate 24 to engage or pass through the alignment holes 20 in the DBS card 10. Each aperture 28 preferably has a diameter that is sufficiently greater than the diameter of a collection region 14 so that the positioning tolerance for the DBS card 10 relative to the plate 24 is less stringent.

In another embodiment, the SPE device further includes a card holder that is configured for attachment to the plate 24, for example, by clamping or by an interference fit between one or more openings in the card holder with one or more features, such as alignment pins 30, on the plate 24. In this embodiment, instead of securing the DBS card directly to the plate 24, the DBS card is secured to the card holder and the card holder is attached to the plate 24. By way of an example, the card holder can be attached to the plate 24 using one or more clamps. The card holder includes apertures configured for proper alignment to the collection regions of the DBS card and the plate apertures 28 when mounted to the plate 24.

Although described above with respect to the dried sample card 10 of FIG. 1, in other embodiments, the SPE device is configured to receive and hold dried sample cards of other types and formats. For example, the SPE device can be used with conventional DBS cards in which the carrier medium does not include impermeable regions to define the collection regions for the samples. Various embodiments of the SPE device are adapted for use with dried sample cards having different shapes, sample locations, numbers of samples and alignment means. Moreover, the dried sample cards can include dried samples of other biological fluids such as urine, saliva, plasma, serum and cerebrospinal fluids.

Figure 3:
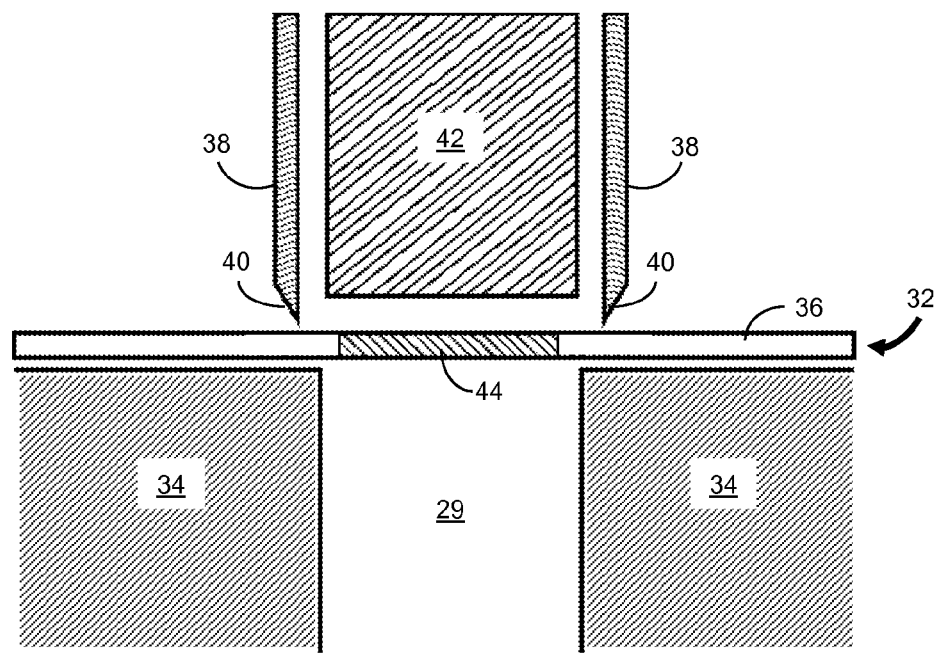
FIG. 3 is a partial cross-sectional illustration of an embodiment of an SPE device and a punch head that utilizes a punch process for generating an extraction sample in accordance with the invention.

FIG. 3 is a partial cross-sectional illustration of an embodiment of an SPE device that utilizes a punch process for generating a punched disc which contains the dried fluid sample to be extracted. The illustration shows a region of the device limited to a single vertical channel 29 and a corresponding DBS 44 on a DBS card 32 although it will be recognized that the device contains one or more other regions defined about other channels 29. The device includes a support block 34 which is used in combination with a cutting blade 38 and a disc-release piston 42. The cutting blade 38 has a tubular shape with a sharp edge 40 adjacent to the DBS card 32. The device also includes a well 26 below the channel 29 as shown, for example, in FIG. 2A and FIG. 2C. In an alternative embodiment, the device includes a cardholder that is placed over the support block 34, or a similar structure having wells, so that the channels 29 are aligned with the wells.

To generate a punched disc containing the dried fluid sample, the cutting blade 38 is extended downward to pierce the carrier medium of the DBS card 32. Sufficient force is applied so that the sharpened edge penetrates the carrier medium to separate a disc-shaped region of the DBS 44 from the DBS card 32. In alternative embodiments, the diameter of the cutting blade 38 can be different. In some embodiments, the diameter is sufficiently large so that the separated disc has a diameter greater than the nominal diameter of the DBS 44. The diameter of the channel 29 is less than the diameter of the separated disc therefore the disc is supported by the support block 34 and remains in position in the DBS card 32. Subsequently, the disc-release piston 42 extends downward through the DBS card 32 so that the disc is pushed from the DBS card 32 into or through the channel 29 and into a well. An extraction solvent is introduced into the channels 29 and passes into the wells holding the released discs.

Figure 4:
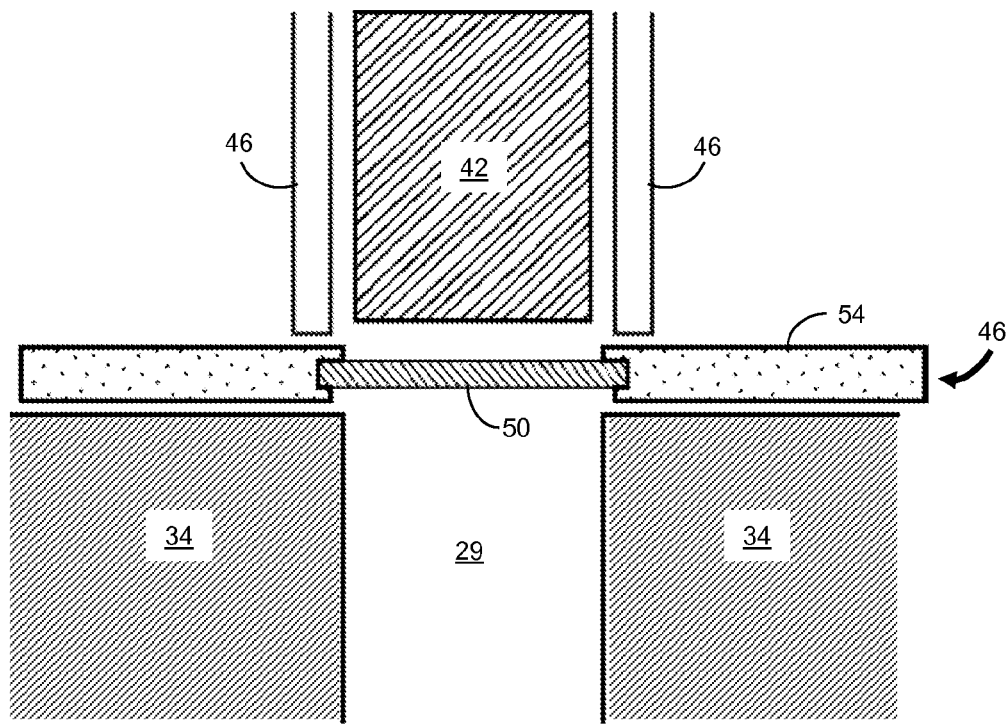
FIG. 4 is a partial cross-sectional illustration of another embodiment of an SPE device and a punch head that utilizes a punch process for generating an extraction sample in accordance with the invention.

FIG. 4 is a cross-sectional illustration of an alternative embodiment of an SPE device showing a region pertaining to a single channel 29 and a collection region 50 of a DBS card 46. The device includes a support block 34 which is used in combination with a disc-release piston 42 and a piston guide 46. Again, the SPE device uses a punch process to generate the punched disc as described for FIG. 3; however, the construction of the DBS card 46 is different. More specifically, the collection regions 50 are pre-cut disc-shaped regions that are held within circular grooves in the surrounding carrier medium 54. Advantageously, the pre-cut collection regions 50 have well-defined volumes that enable whole spot sampling to reduce or eliminate inaccuracies.

An extraction sample is generated by extending the disc-release piston 42 from the base of the piston guide 46 so that the pre-cut collection region 50 is pushed from the surrounding impermeable region 54 and into or through the vertical channel 29 and into a well. Subsequently, a chromatographic solvent is introduced into the channels 29 and passes through to the wells containing the punched collection regions.

The illustrated SPE device can also be used with other types of DBS cards. In one example, the collection regions may be integral to the carrier medium. For example, the DBS card is pre-scored with a circular pattern surrounding each collection region. During the punch process, each disc-release piston 42 moves downward from the piston guide 46 and through the DBS card to release the pre-scored region containing the DBS.

Figure 5:
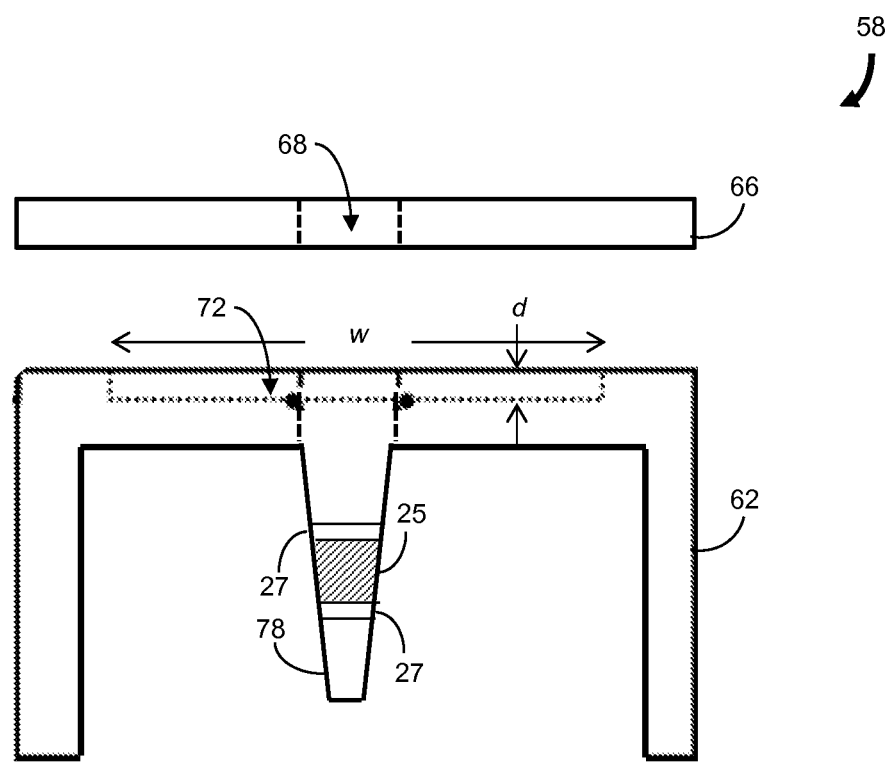
FIG. 5 is a cross-sectional illustration of another embodiment of an SPE device.

FIG. 5 is a cross-sectional illustration of another embodiment of an SPE device 58 for a dried sample card. The device 58 includes an SPE cartridge block 62 and a top plate 66 (i.e., cap). The SPE cartridge block 62 includes a recessed region 72 that receives the DBS card and serves to align the collection regions to the vertical channels 74 that extend through the block 62. Preferably, the recessed region 72 has a depth d that is equal to or greater than the thickness of the DBS card and a length (not shown) and width w that are slightly greater than the length and width of the DBS card. The illustrated device 58 includes wells 78. In the various embodiments, each well 78 includes a sample preparation material, such as a chromatographic sorbent, disposed between a pair of porous filters 27.

A user secures the DBS card in the device 58 by placing the card in the recessed region 72 and gently pressing downward. Optionally, the DBS card can be removed from the cartridge block 62, for example, by inserting a thin tool between the edge of the dried sample card and the bottom surface of the recessed region 72, and prying the dried sample card upward away from the block 62. In one alternative embodiment of the SPE device, a slot is provided in the SPE cartridge block into which the DBS card is inserted.

The two side walls and the end wall of the slot constrain the DBS card to the desired position relative to the SPE cartridge block.

In the illustrated embodiment, the top plate 66 includes one or more apertures, or openings, 68 between its upper and lower surfaces. Once the DBS card is inserted into the recessed region 72, the top plate 66 is secured to the top of the SPE cartridge block 62 so that the one or more openings 68 expose the collection regions of the DBS card. By way of specific examples, the top plate 66 can be secured to the SPE cartridge block 62 using one or more latches or clamps, or by snapping onto the block 62 using an interference fit with one or more features on the top plate 66 or block 62. In an alternative embodiment, the top plate 66 is attached to the SPE cartridge block 62 using one or more hinges that allow the top plate 66 to pivot into a closed position to cover the DBS card and, optionally, to pivot to an open position to allow retrieval of the DBS card from the recessed region 72.

To start the extraction process, a DBS card is secured in position in the SPE cartridge block 62 and then the top plate 66 is secured in place on the top of the block 62. A separate piston block (not shown) can be placed on top of or near to the top plate 66 so that disc-release pistons are aligned with the wells 78 and collection regions of the DBS card. The pistons are then operated in a manner similar to that described for the devices of FIG. 3 or FIG. 4. The pistons pass through the one or more openings 68 in the top plate 66 and release punched regions of the DBS card into the wells 78.

The extraction process continues by passing an extraction solvent through the one or more openings in the top plate 66 and the openings created in the DBS card by the punch process. The solvent passes into each well 78 where it is used to generate the extraction samples, i.e., reconstitute the fluid samples, from the punched regions. In an alternative process, the top plate 66 and punched DBS card can be removed from the SPE cartridge block 62 prior to providing the solvent to the wells 78 containing the punched discs. Each reconstituted sample passes through the chromatographic sorbent 25 in the well 78 where removal of one or more constituents of the extraction sample occurs. Upon reaching the outlet end of the wells, these constituents can be further processed or used directly for quantitative analysis.

Figure 6:
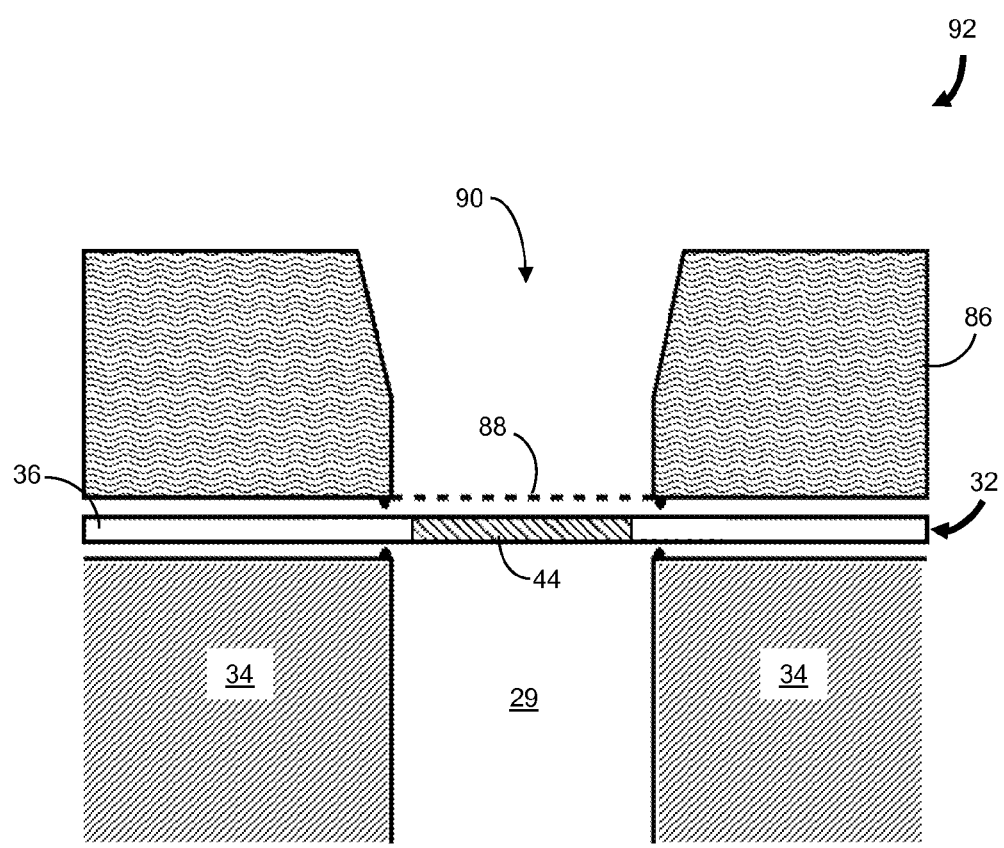
FIG. 6 is a partial cross-sectional illustration of an embodiment of an SPE device that utilizes a flow-through process for generating an extraction sample.

Various flow-through extractions techniques for generating extraction samples are known. For example, PCT Patent Application Publication No. WO/2011/153122 (referenced above) describes flow-through extraction modules and processes that can be used to create extraction samples from dried sample cards. FIG. 6 is a partial cross-sectional illustration of an embodiment of an SPE device 92 that can utilize such flow-through techniques in a solid phase extraction process. The illustration shows a region of the SPE device 92 corresponding to a single channel 29 and a corresponding DBS 44 on a DBS card 32. The device 92 includes a support block 34 having a plurality of vertical channels 29 therein, a solvent reservoir block 86 and, optionally, a wetting barrier membrane 88. By way of example, the membrane 88 can be a Teflon membrane that does not pass liquid under ambient conditions but does allow liquid at sufficient pressure to pass through the membrane 88. A plurality of wells 90 each adapted to hold a solvent are formed in the solvent reservoir block 86 and are aligned with a respective DBS 44 or collection region in the DBS card prior to the start of the sample extraction process.

To generate extraction samples, an extraction solvent is dispensed into each solvent well 90. Subsequently, a positive-pressure manifold is coupled to the device to generate a sufficient pressure gradient for the extraction solvent to flow through the membrane 88 and DBS 44. Alternatively, the device 92 can be coupled to a vacuum device or centrifuge module to create sufficient pressure to flow the extraction solvent through the membrane 88 and DBS 44. Subsequently, each extraction sample passes through a sample preparation material, such as a chromatographic solvent, to remove at least one constituent from the extraction sample.

Typical DBS processes include experimentation with multiple extraction conditions during the method development step because each analyte has a different solubility according to the particular extraction solvent. Moreover, it is desirable to use a minimal volume of the extraction solvent to increase the analysis sensitivity. If a large volume of extraction solvent is used for analyte extraction, an additional process to reduce the extraction sample volume, for example, increasing analyte concentration using an evaporative technique is often performed prior to LC-MS analysis. To address these complications, the extraction solvent used with the embodiments described above can be of different forms. For example, the extraction solvent can be a supercritical fluid with a high solvating capacity similar to a liquid. Alternatively, the extraction solvent can be a subcritical fluid or a solvent having a high $CO_2$ level. The capability of a rapid phase transfer is useful for efficient sample concentration by collecting the analytes onto a sorbent or into a liquid prior to LC-MS analysis.

Figure 7:
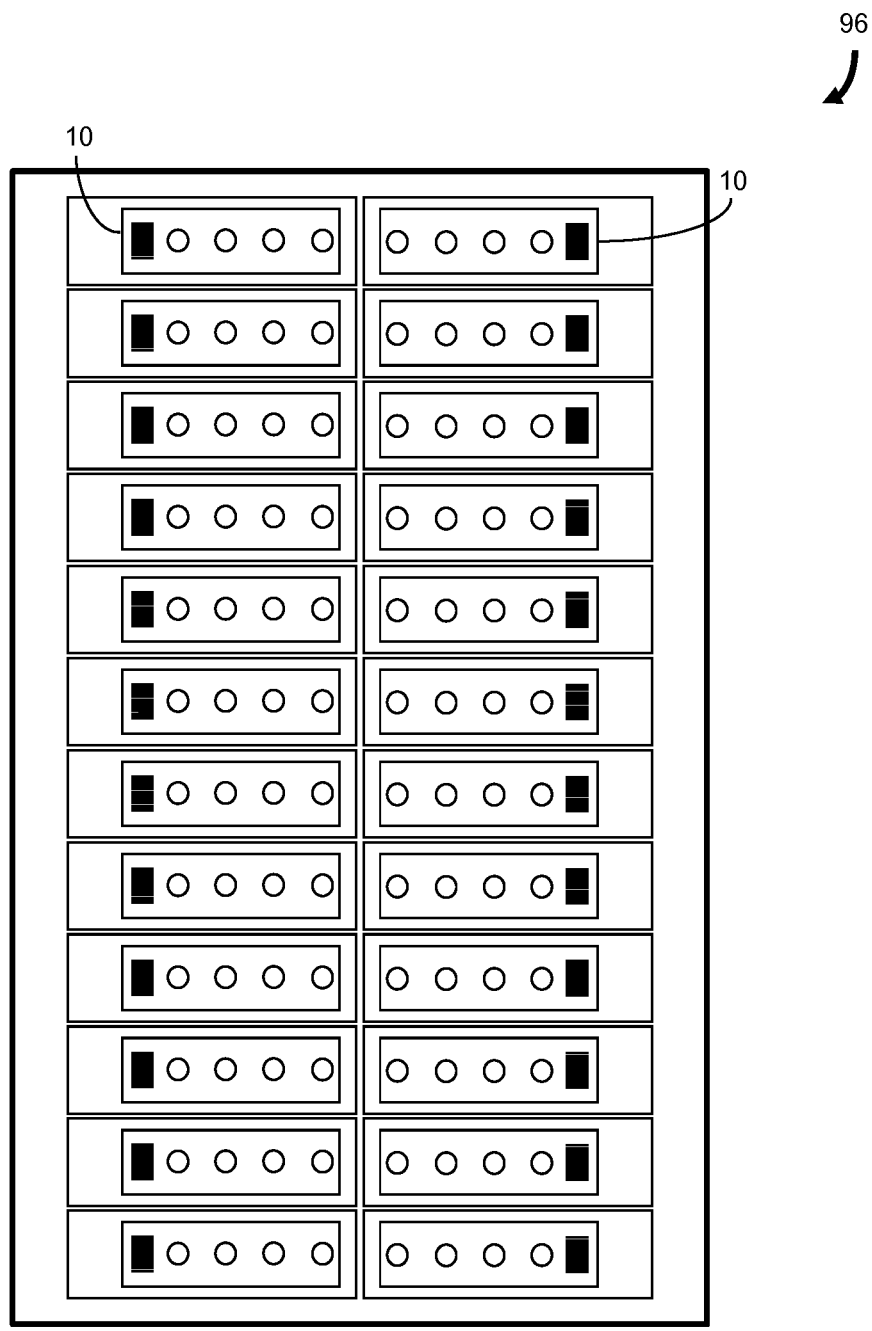
FIG. 7 is a top view illustration of an embodiment of an SPE device loaded with a plurality of dried sample cards in accordance with the invention.

In the embodiments described above, each SPE device receives a single dried sample card. In alternative embodiments, the SPE devices are configured to receive a plurality of dried sample cards. By way of example, an SPE device 96 can be configured to accept 24 dried sample cards 10 each having a 1×4 arrangement of dried samples so that the dried sample cards 10 are arranged as twelve rows by two columns to create an array of 8×12 dried samples as shown in FIG. 7. It should be recognized that various other multi-card configurations are possible for the SPE device.

While the invention has been shown and described with reference to specific embodiments, it should be understood by those skilled in the art that various changes in form and detail may be made therein without departing from the spirit and scope of the invention as recited in the accompanying claims.

What is claimed is:

1. A device for solid phase extraction of a dried sample of a biological fluid, comprising:
 a support structure having a first side to receive a dried sample card having a plurality of dried samples of a biological fluid, the support structure having a second side opposite the first side and having a plurality of apertures between the first side and the second side, the support structure configured to align and secure the dried sample card in a position wherein each of the dried samples is adjacent to one of the apertures;
 a plurality of wells each having an inlet end at one of the apertures on the second side of the support structure and having an outlet end; and
 a sample preparation material disposed in at least one of the wells.

2. The device of claim 1 wherein the sample preparation material is a chromatographic sorbent.

3. The device of claim 1 further comprising, for each of the wells having a sample preparation material, a pair of porous filters with the sample preparation material disposed therebetween.

4. The device of claim 1 further comprising at least one alignment pin extending from the sample side of the support structure and configured to engage an alignment hole in the dried sample card.

5. The device of claim 1 further comprising a card holder attached to the first side of the support structure, the card holder having a first side to receive the dried sample card and a second side adjacent to the first side of the support structure.

6. The device of claim 5 further comprising at least one clamp configured to attach the card holder to the first side of the support structure.

7. The device of claim 5 further comprising at least one alignment pin extending from the first side of the support structure to engage an opening in the card holder.

8. A method for solid phase extraction of a dried sample of a biological fluid, the method comprising:
   securing a dried sample card having a plurality of dried samples of a biological fluid to a solid phase extraction device, the solid phase extraction device comprising:
      a support structure having a first side to receive a dried sample card having a plurality of dried samples of a biological fluid, the support structure having a second side opposite the first side and having a plurality of apertures between the first side and the second side, the support structure configured to align and secure the dried sample card in a position wherein each of the dried samples is adjacent to one of the apertures;
      a plurality of wells each having an inlet end at one of the apertures on the second side of the support structure and having an outlet end; and
      a sample preparation material disposed in each of the wells;
   for each of the dried samples and a respective one of the wells, flowing an extraction solvent through the dried sample and into the well to thereby generate an extraction sample; and
   for each of the extraction samples, passing the extraction sample through the sample preparation material in the well to remove at least one constituent from the extraction sample.

9. The method of claim 8 wherein flowing the extraction solvent comprises applying a pressure differential across the solid phase extraction device.

10. A method for solid phase extraction of a dried sample of a biological fluid, the method comprising:
   securing a dried sample card having a plurality of dried samples of a biological fluid to a solid phase extraction device, the solid phase extraction device comprising:
      a support structure having a first side to receive a dried sample card having a plurality of dried samples of a biological fluid, the support structure having a second side opposite the first side and having a plurality of apertures between the first side and the second side, the support structure configured to align and secure the dried sample card in a position wherein each of the dried samples is adjacent to one of the apertures;
      a plurality of wells each having an inlet end at one of the apertures on the second side of the support structure and having an outlet end; and
      a sample preparation material disposed in each of the wells;
   separating portions of the dried sample card from a remainder of the dried sample card to cause each of the dried samples to be disposed in one of the wells;
   supplying an extraction solvent to each of the wells to thereby create extraction samples; and
   for each of the extraction samples, passing the extraction sample through the sample preparation material in the well to remove at least one constituent from the extraction sample.

11. The method of claim 10 wherein the extraction solvent is supplied through openings in the dried sample card at locations where the separated portions were formed.

* * * * *